(12) United States Patent
Knudson et al.

(10) Patent No.: US 6,742,524 B2
(45) Date of Patent: *Jun. 1, 2004

(54) METHOD AND APPARATUS TO TREAT CONDITIONS OF THE NASO-PHARYNGEAL AREA

(75) Inventors: Mark B. Knudson, Shoreview, MN (US); Katherine S. Tweden, Mahtomedi, MN (US); Timothy R. Conrad, Eden Prairie, MN (US)

(73) Assignee: Restore Medical, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/394,887

(22) Filed: Mar. 21, 2003

(65) Prior Publication Data

US 2003/0140930 A1 Jul. 31, 2003

Related U.S. Application Data (63) Continuation of application No. 10/190,183, filed on Jul. 3, 2002, now Pat. No. 6,546,936, which is a continuation of application No. 09/636,803, filed on Aug. 10, 2000, now Pat. No. 6,431,174.

(51) Int. Cl.[7] .......................... A61B 13/00; A61F 13/00
(52) U.S. Cl. ........................................ 128/898; 424/434
(58) Field of Search ........................... 128/898, 897, 128/200.243, 200.24, 848, 846, 859–862; 424/434, 423; 523/115; 602/902; 623/23.73, 11.11, 14.11; 600/12

(56) References Cited

U.S. PATENT DOCUMENTS

| | | | |
|---|---|---|---|
| 3,998,209 A | 12/1976 | Macvaugh | |
| 4,803,075 A | 2/1989 | Wallace et al. | |
| 4,830,008 A | 5/1989 | Meer | |
| 4,978,323 A | 12/1990 | Freedman | |
| 5,046,512 A | 9/1991 | Murchie | |
| 5,052,409 A | 10/1991 | Tepper | |
| 5,133,354 A | 7/1992 | Kallok | |
| 5,176,618 A | 1/1993 | Freedman | |
| 5,178,156 A | 1/1993 | Takishima et al. | |
| 5,190,053 A | 3/1993 | Meer | |

(List continued on next page.)

FOREIGN PATENT DOCUMENTS

| | | |
|---|---|---|
| DE | 44 12 190 A1 | 10/1995 |
| DE | 199 20 114 A1 | 11/2000 |
| EP | 0 292 936 A2 | 11/1988 |
| EP | 0 706 808 A1 | 4/1996 |
| SU | 1553140 | 3/1990 |
| WO | WO 00/59398 | 10/2000 |
| WO | WO 01/19301 A1 | 3/2001 |
| WO | WO 01/23039 A1 | 4/2001 |

OTHER PUBLICATIONS

Brochure, "Haven't you suffered from Snoring long enough", *Somnoplasty*[SM], 2 pgs.
Brochure, "Our Diagnostic Procedures are a Snap®!", *Snap Laboratories*, 4 pgs.
Brochure, "Snore–Free Nights—Guaranteed!", *Your Health News*, 2 pgs.

(List continued on next page.)

*Primary Examiner*—Mary Beth Jones
*Assistant Examiner*—Nikita R Veniaminov
(74) *Attorney, Agent, or Firm*—Merchant & Gould P.C.

(57) ABSTRACT

A patient's upper airway condition such as snoring and sleep apnea is treated by selecting a particulate material selected for limited migration within tissue and for encouraging a fibrotic response of tissue to the material. A bolus of the particulate material is injected into the tissue area to structurally stiffen the tissue.

11 Claims, 6 Drawing Sheets

U.S. PATENT DOCUMENTS

| | | | |
|---|---|---|---|
| 5,204,382 A | 4/1993 | Wallace et al. | |
| 5,258,028 A | 11/1993 | Ersek et al. | |
| 5,281,219 A | 1/1994 | Kallok | |
| 5,284,161 A | 2/1994 | Karell | |
| 5,451,406 A | 9/1995 | Lawin et al. | |
| 5,456,662 A | 10/1995 | Edwards et al. | |
| 5,514,131 A | 5/1996 | Edwards et al. | |
| 5,540,733 A | 7/1996 | Testerman et al. | |
| 5,582,184 A | 12/1996 | Erickson et al. | |
| 5,591,216 A | 1/1997 | Testerman et al. | |
| 5,669,377 A | 9/1997 | Fenn | |
| 5,674,191 A | 10/1997 | Edwards et al. | |
| 5,718,702 A | 2/1998 | Edwards | |
| 5,792,067 A | 8/1998 | Karell | |
| 5,792,478 A | 8/1998 | Lawin et al. | |
| 5,843,021 A | 12/1998 | Edwards et al. | |
| RE36,120 E | 3/1999 | Karell | |
| 5,897,579 A | 4/1999 | Sanders | |
| 5,922,006 A | 7/1999 | Sugerman | |
| 5,983,136 A | 11/1999 | Kamen | |
| 6,250,307 B1 | 6/2001 | Conrad et al. | |
| 6,390,096 B1 | 5/2002 | Conrad et al. | |
| 6,401,717 B1 | 6/2002 | Conrad et al. | |
| 6,415,796 B1 | 7/2002 | Conrad et al. | |
| 6,431,174 B1 | 8/2002 | Knudson et al. | |
| 6,439,238 B1 | 8/2002 | Brenzel et al. | |
| 6,450,169 B1 | 9/2002 | Conrad et al. | |
| 6,453,905 B1 | 9/2002 | Conrad et al. | |
| 6,502,574 B2 | 1/2003 | Stevens et al. | |
| 6,513,530 B2 | 2/2003 | Knudson et al. | |
| 6,513,531 B2 | 2/2003 | Knudson et al. | |
| 6,516,806 B2 | 2/2003 | Knudson et al. | |
| 6,523,541 B2 | 2/2003 | Knudson et al. | |
| 6,523,542 B2 | 2/2003 | Knudson et al. | |
| 6,523,543 B2 | 2/2003 | Conrad et al. | |
| 6,546,936 B2 * | 4/2003 | Knudson et al. | 128/898 |
| 2001/0025642 A1 | 10/2001 | Conrad et al. | |
| 2001/0044587 A1 | 11/2001 | Conrad et al. | |
| 2002/0035994 A1 | 3/2002 | Stevens et al. | |
| 2002/0056462 A1 | 5/2002 | Conrad et al. | |
| 2002/0108618 A1 | 8/2002 | Conrad et al. | |

OTHER PUBLICATIONS

Brochure, "Snoreless™", *Nutrition for Life International*, 2 pgs. (Dec. 1999).

Boot, H. et al., "Long–Term Results of Uvulopalatopharyngoplasty for Obstructive Sleep Apnea Syndrome", *The Laryngoscope*, pp. 469–475 (Mar. 2000).

Cole, P. et al., "Snoring: A Review and a Reassessment", *The Journal of Otolaryngology*, vol. 24, No. 5, pp. 303–306 (1995).

Coleman, S. et al., "Midline Radiofrequency Tissue Reduction of the Palate for Bothersome Snoring and Sleep–Disordered Breathing: A Clinical Trial", *Otolaryngology—Head and Neck Surgery*, pp. 387–394 (Mar. 2000).

Dalmasso, F. et al., "Snoring: analysis, measurement, clinical implications and applications", *Eur. Respir. J.*, vol. 9, pp. 146–159 (1996).

Ellis, P. D. M. et al., "Surgical relief of snoring due to palatal flutter: a preliminary report", *Annals of the Royal College of Surgeons of England*, vol. 75, No. 4, pp. 286–290 (1993).

Fischer, Y. et al., "Die Radiofrequenzablation des weichen Gaumens (Somnoplastik)", *Redaktion*, pp. 33–40 (2000).

Gillette, P. et al., "Pediatric Cardiac Pacing", *Cardiology Clinics*, vol. 10, No. 4, pp. 749–754 (Nov. 1992).

Harries, P.G. et al., "Review Article: The surgical treatment of snoring", *The Journal of Laryngology and Otology*, vol. 110, pp. 1105–1106 (Dec. 1996).

Huang, L., "Flutter of Cantilevered Plates in Axial Flow", *Journal of Fluids and Structures*, vol. 9, pp. 127–147 (1995).

Huang, L. et al., "Biomechanics of snoring", *Endeavour*, vol. 19, No. 3, pp. 96–100 (1995).

Kasey, K. et al., "Radiofrequency Volumetric Reduction of the Palate: An Extended Follow–Up Study", *Otolaryngology—Head and Neck Surgery*, vol. 122, No. 3, pp. 410–414 (Mar. 2000).

LaFrentz, J.R.L. et al., "Palatial stiffening techniques for snoring in a novel canine model", *ARO Abstracts*, vol. 22, Abstrct No. 499, pp. 125–126 (Feb. 13–18, 1999).

Lemperle, G., et al., "PMMA Microspheres (Artecoll) for Skin and Soft–Tissue Augmentation. Part II: Clinical Investigations", *Plastic and Reconstructive Surgery*, pp. 627–634 (Sep. 1995).

C. Lorenz, "If he Snores—what can you do about it?", Today's Woman, Jul. 1948, p. 112.

Schwartz, R.S. et al., "Effects of electrical stimulation to the soft palate on snoring and obstructive sleep apnea", *J. Prosthet. Dent.*, vol. 76, No. 3, pp. 273–281 (1996).

Wiltfang, J. et al., "First results on daytime submadibular electrostimulation of suprahyoidal muscles to prevent night–time hypopharyngeal collapse in obstructive sleep apnea syndrome", *Int. J. Oral Maxillofac. Surg.*, vol. 28, pp. 21–25 (1999).

Blumen et al., Radiofrequency Ablation for the Treatment of Mild to Moderate Obstructive Sleep Apnea, Nov., 2002; pp. 2086–2092.

* cited by examiner

METHOD AND APPARATUS TO TREAT CONDITIONS OF THE NASO-PHARYNGEAL AREA

This application is a continuation of application Ser. No. 10/190,183, filed Jul. 3, 2002, now is U.S. Pat. No. 6,546,936 which is a continuation of 09/636,803, filed Aug. 10, 2000, now U.S. Pat. No. 6,431,174, which applications are incorporated herein by reference.

BACKGROUND

1. Field of the Invention

This invention is directed to methods and apparatuses for treating conditions of the naso-pharyngeal area such as snoring and sleep apnea. More particularly, this invention pertains to method and apparatus to stiffen tissue of the naso-pharyngeal area.

2. Description of the Prior Art

Snoring has received increased scientific and academic attention. One publication estimates that up to 20% of the adult population snores habitually. Huang, et al., "Biomechanics of Snoring", *Endeavour*, p. 96–100, Vol. 19, No. 3 (1995). Snoring can be a serious cause of marital discord. In addition, snoring can present a serious health risk to the snorer. In 10% of habitual snorers, collapse of the airway during sleep can lead to obstructive sleep apnea syndrome. Id.

Notwithstanding numerous efforts to address snoring, effective treatment of snoring has been elusive. Such treatment may include mouth guards or other appliances worn by the snorer during sleep. However, patients find such appliances uncomfortable and frequently discontinue use (presumably adding to marital stress).

Electrical stimulation of the soft palate has been suggested to treat snoring and obstructive sleep apnea. See, e.g., Schwartz, et al., "Effects of electrical stimulation to the soft palate on snoring and obstructive sleep apnea", *J. Prosthetic Dentistry*, pp. 273–281 (1996). Devices to apply such stimulation are described in U.S. Pat. Nos. 5,284,161 and 5,792,067. Such devices are appliances requiring patient adherence to a regimen of use as well as subjecting the patient to discomfort during sleep. Electrical stimulation to treat sleep apnea is discussed in Wiltfang, et al., "First results on daytime submandibular electrostimulation of suprahyoidal muscles to prevent night-time hypopharyngeal collapse in obstructive sleep apnea syndrome", *International Journal of Oral & Maxillofacial Surgery*, pp. 21–25 (1999).

Surgical treatments have been employed. One such treatment is uvulopalatopharyngoplasty. In this procedure, so-called laser ablation is used to remove about 2 cm of the trailing edge of the soft palate thereby reducing the soft palate's ability to flutter between the tongue and the pharyngeal wall of the throat. The procedure is frequently effective to abate snoring but is painful and frequently results in undesirable side effects. Namely, removal of the soft palate trailing edge comprises the soft palate's ability to seal off nasal passages during swallowing and speech. In an estimated 25% of uvulopalatopharyngoplasty patients, fluid escapes from the mouth into the nose while drinking. Huang, et al., supra at 99. Uvulopalatopharyngoplasty (UPPP) is also described in Harries, et al., "The Surgical treatment of snoring", *Journal of Laryngology and Otology*, pp. 1105–1106 (1996) which describes removal of up to 1.5 cm of the soft palate. Assessment of snoring treatment is discussed in Cole, et al., "Snoring: A review and a Reassessment", *Journal of Otolaryngology*, pp. 303–306 (1995).

Huang, et al., supra, describe the soft palate and palatal snoring as an oscillating system which responds to airflow over the soft palate. Resulting flutter of the soft palate (rapidly opening and closing air passages) is a dynamic response generating sounds associated with snoring. Huang, et al., propose an alternative to uvulopalatopharyngoplasty. The proposal includes using a surgical laser to create scar tissue on the surface of the soft palate. The scar is to reduce flexibility of the soft palate to reduce palatal flutter. Huang, et al., report initial results of complete or near-complete reduction in snoring and reduced side effects.

Surgical procedures such as uvulopalatopharyngoplasty and those proposed by Huang, et al., continue to have problems. The area of surgical treatment (i.e., removal of palatal tissue or scarring of palatal tissue) may be more than is necessary to treat the patient's condition. Surgical lasers are expensive. The proposed procedures are painful with drawn out and uncomfortable healing periods. The procedures have complications and side effects and variable efficacy (e.g., Huang, et al., report promising results in 75% of patients suggesting a full quarter of patients are not effectively treated after painful surgery). The procedures may involve lasting discomfort. For example, scar tissue on the soft palate may present a continuing irritant to the patient. Importantly, the procedures are not reversible in the event they happen to induce adverse side effects not justified by the benefits of the surgery.

In pharyngeal snoring, the pharyngeal airway collapses in an area between the soft palate and the larynx. One technique for treating airway collapse is continuous positive airway pressure (CPAP). In CPAP air is passed under pressure to maintain a patent airway. However, such equipment is bulky, expensive and generally restricted to patients with obstructive sleep apnea severe enough to threaten general health. Huang, et al. at p. 97.

A technique for snoring treatment is disclosed in commonly assigned and copending U.S. patent applications Ser. No. 09/513,432 filed Feb. 25, 2000. According to certain embodiments of that application, permanent implants are placed in the soft palate to add stiffness to the soft palate.

SUMMARY OF THE INVENTION

According to one aspect of the present invention, methods and apparatuses are disclosed for treating a patient's upper airway condition such as snoring and sleep apnea. The invention includes selecting a particulate material selected for limited migration within tissue and for encouraging a fibrotic response of tissue to the material. A bolus of the particulate material is injected into the tissue area to structurally stiffen the tissue.

DESCRIPTION OF THE PREFERRED EMBODIMENT

A. Physiology Background

Referring now to the several drawing figures, in which identical elements are numbered identically throughout, a description of a preferred embodiment of the present invention will now be provided.

Figure 1:
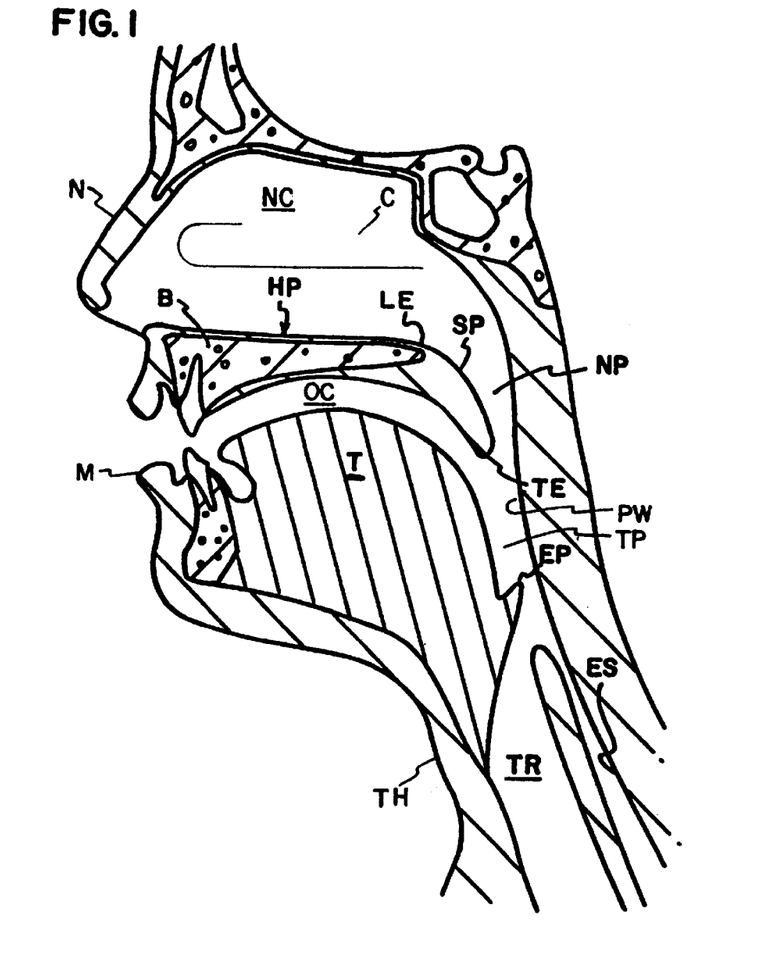
FIG. 1 shows, in cross-section, a naso-pharyngeal area of an untreated patient.
Figure 2:
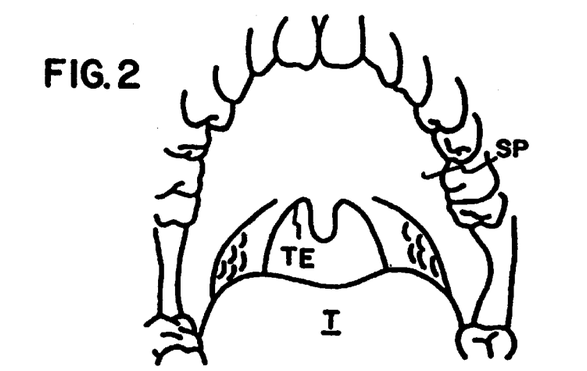
FIG. 2 shows a soft palate viewed through an open mouth of the untreated patient of FIG. 1.

FIG. 1 shows, in cross-section, a naso-pharyngeal area of an untreated patient. FIG. 2 shows a soft palate SP viewed through an open mouth of the untreated patient. FIG. 1 shows the nose N, mouth M and throat TH. The tongue T is shown in an oral cavity OC of the mouth. A hard palate HP (containing a bone B) separates the oral cavity OC from the nasal cavity NC. The nasal concha C (soft tissue which defines, in part, the nasal sinus—not shown) resides in the nasal cavity NC.

The soft palate SP (a muscle activated soft tissue not supported by bone) depends in cantilevered manner at a leading end LE from the hard palate HP and terminates at a trailing end TE. Below the soft palate SP, the pharyngeal wall PW defines the throat passage TP. A nasal passage NP connects the nasal cavity NC to the pharyngeal wall PW. Below an epiglottis EP, the throat passage TP divides into a trachea TR for passing air to the lungs and an esophagus ES for passing food and drink to the stomach.

The soft palate SP is operated by muscles (not separately shown and labeled) to lift the soft palate SP to urge the trailing edge TE against the rear area of the pharyngeal wall PW. This seals the nasal cavity NC from the oral cavity OC during swallowing. The epiglottis EP closes the trachea TR during swallowing and drinking and opens for breathing.

For purposes of this disclosure, the nasal cavity NC, oral cavity OC and throat passage TP are collectively referred to as the naso-pharyngeal area of the patient with the area including the various body surfaces which cooperate to define the nasal cavity NC, oral cavity OC and throat passage TP. These body surfaces include outer surfaces of the nasal concha C, the upper and lower surfaces of the soft palate SP and outer surfaces of the pharyngeal wall PW. Outer surfaces means surfaces exposed to air. Both the upper and lower surfaces of the soft palate SP are outer surfaces.

Snoring can result from vibration of any one of a number of surfaces or structures of the naso-pharyngeal area. Most commonly, snoring is attributable to vibration of the soft palate SP. However, vibratory action of the nasal concha C and the pharyngeal wall PW can also contribute to snoring sounds. It is not uncommon for vibratory action from more than one region of the naso-pharyngeal area to contribute to snoring sounds. Sleep apnea can result from partial or full collapse of the naso-pharyngeal wall during sleep.

While most of the present discussion will describe placing a stiffening implant in the soft palate SP, it will be appreciated the present invention is applicable to other regions of the naso-pharyngeal area including the nasal concha C and the pharyngeal wall PW.

The snoring sound is generated by impulses caused by rapid obstruction and opening of airways. Huang, et al., state the airway passage opening and closing occurs 50 times per second during a snore. Huang, et al., utilize a spring-mass model (FIG. 5) to illustrate oscillation of the soft palate in response to airflow (where the soft palate is the ball B of mass depending by a spring S from a fixed anchor A).

Figure 3:
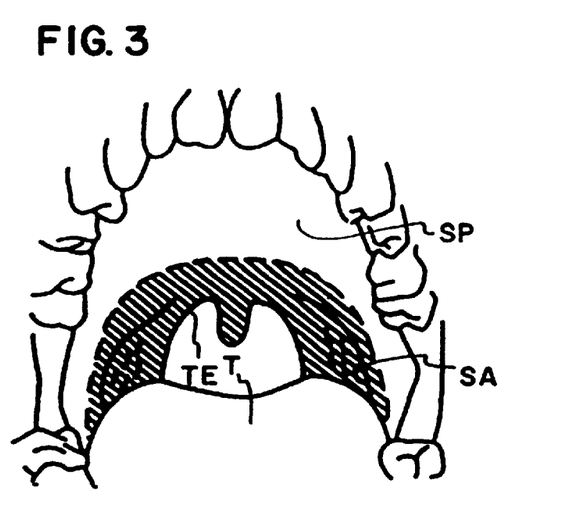
FIG. 3 is a front view of an interior of the mouth shown in FIG. 1 and showing an area to be ablated according to a first prior art surgical procedure.
Figure 4:
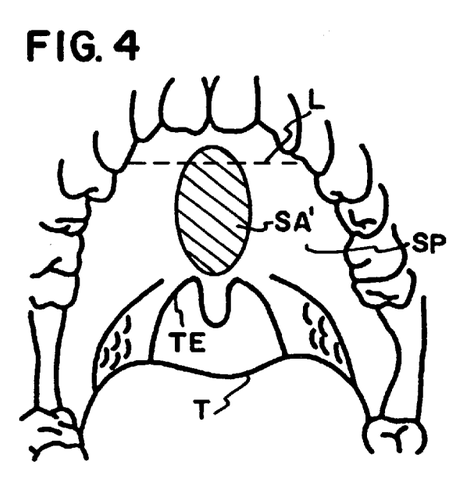
FIG. 4 is the view of FIG. 3 and showing an area to be scarred according to a second prior art surgical procedure.

Huang, et al., analogize the shortening of the soft palate SP in uvulopalatopharyngoplasty as effectively raising the critical air flow speed at which soft palate flutter will occur. The shaded area SA in FIG. 3 shows the area of the trailing end TE of the soft palate SP to be removed during this procedure. The alternative procedure proposed by Huang, et al., reduces the flexibility of the soft palate SP through surface scarring which is asserted as effecting the critical flow speed. The shaded area SA' in FIG. 4 shows the area to be scarred by this alternate procedure. In FIG. 4, dashed line L shows the demarcation between the soft and hard palates.

Figure 5:
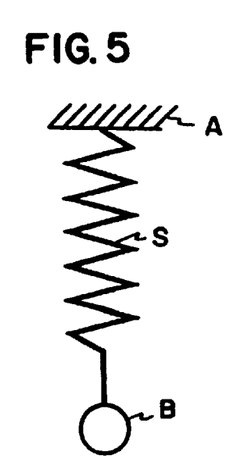
FIG. 5 is a schematic representation of a spring-mass system model of the soft palate.

Using the spring-mass model of FIG. 5 as a convenient model of the soft palate SP, the present invention is directed to a surgical implant into the soft palate SP to alter the elements of the model and thereby alter the dynamic response of the soft palate SP to airflow. The implant can alter the mass of the model (the ball B of FIG. 5), the spring constant of the spring S, the dampening of the spring S or any combination of these elements. Unlike the prior art surgical techniques, the implants that will be described are easy to insert in a small incision resulting in reduced patient discomfort and are not exposed to the interior of the mouth (such as the surface scarring of Huang, et al.) as a patient irritant. Also, as will be described, the degree of dynamic remodeling can be fine tuned avoiding the need for excessive anatomical modification and are reversible in the event of adverse consequences.

B. Disclosure of Copending Applications

For purposes of illustrative background, FIGS. 6–15 and the related text below describe certain embodiments of inventions disclosed in the afore-mentioned U.S. patent application Ser. No. 09/513,432.

Figure 6:
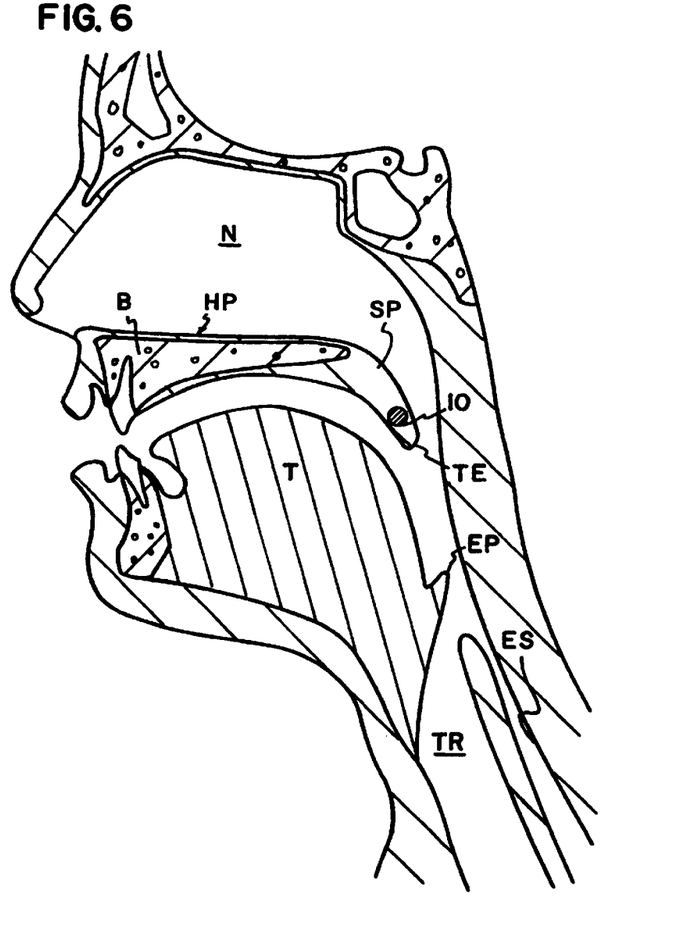
FIG. 6 is the view of FIG. 1 with the soft palate containing an implant in the form of a unit of mass.
Figure 7:
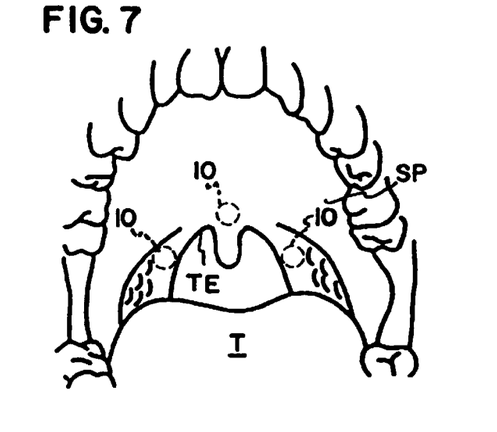
FIG. 7 is the view of FIG. 3 showing the unit of mass of FIG. 6.

FIGS. 6–7 illustrate an embodiment where individual units 10 of mass (in the form of implantable modular devices such as spheres or implants of other geometry) are imbedded in the soft palate SP in close proximity to the trailing end TE. With reference to the model of FIG. 5, the spheres add mass to the mass-spring system thereby altering dynamic response to airflow and adding resistance to displacement and accelerating. The modules are described as any bio-compatible material such as titanium or ceramic.

The spheres may be sintered or otherwise provided with tissue growth inducing material on their outer surface. Such material permits and encourages tissue in-growth to secure the implant 10 in place. Also, placement of an implant 10 will induce a fibrotic response acting to stiffen the soft palate SP (and further alter the dynamic response and resistance to displacement and acceleration). A sintered or coated sphere 10 will enhance the fibrotic response and resulting stiffening.

In addition to modifying the mass profile of the spring-mass system, the spring component S of FIG. 5 can be modified (alone or in combination with mass modification) to alter dynamic response. FIGS. 8–11 illustrate an implant 20 in the form of a flexible strip for placement in the soft palate. The use of the term "strip" is not limited to long, narrow implants but can also includes plates or other geometries implanted to alter the dynamic model of the soft palate SP.

Figure 8:
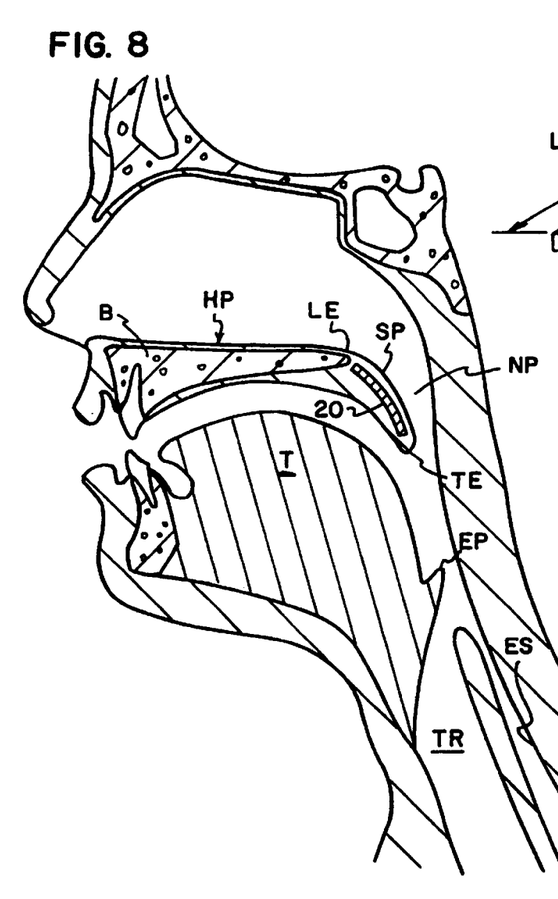
FIG. 8 is the view of FIG. 6 with the soft palate containing an implant in the form of a longitudinal member.
Figure 9:
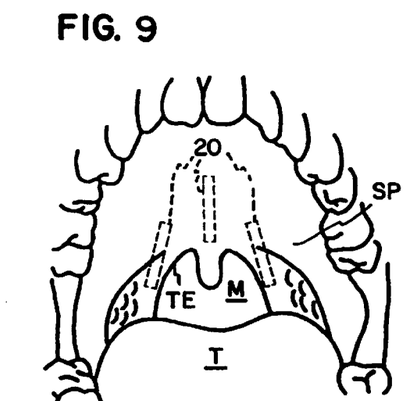
FIG. 9 is the view of FIG. 7 showing the implant of FIG. 8.
Figure 10:
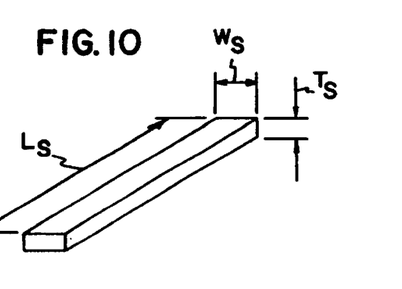
FIG. 10 is a perspective view of the implant of FIG. 8.

The strip 20 has a transverse dimension less than a longitudinal dimension. By way of non-limiting example, the strip may have a length $L_s$ of about 20–30 mm, a thickness $T_s$ of about 2–4 mm and a width $W_s$ of 5–10 mm. As shown in FIG. 8, the strip 20 is embedded in the soft palate SP with the longitudinal dimension $L_s$ extending from adjacent the hard palate HP toward the trailing end TE of the soft palate SP. As shown in FIG. 9, multiple strips 20 may be embedded in the soft palate SP extending either straight rearward or angled to the sides while extending rearward.

Such stiffening of the soft palate SP stiffens and dampens the spring S in the spring-mass system of FIG. 5 and alters the dynamic response of the soft palate SP. The strip 20 may be a spring having a spring constant to further resist deflection of the soft palate SP as well as urging the soft palate SP to the relaxed state of FIG. 5. The stiffness of the strip 20, a spring constant of the strip 20, and the number of strips 20, are selected to avoid preclusion of closure of the soft palate SP during swallowing. Examples of suitable materials include titanium and nitinol (a well-known nickel-titanium alloy). As with the examples of FIGS. 9 and 10, the strips 20 may be provided with tissue in-growth surfaces or may be coated as desired.

Figure 11:
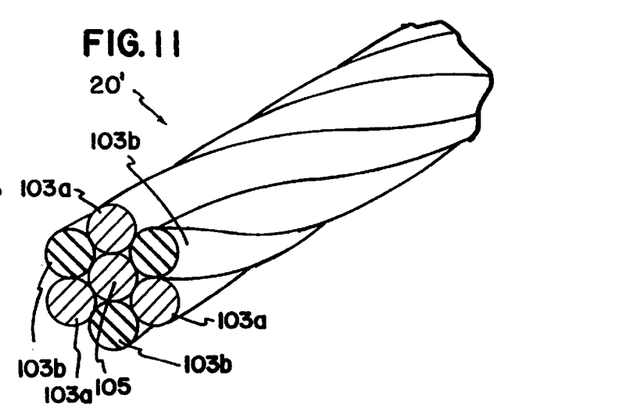
FIG. 11 is a perspective view of a braided implant.

FIG. 11 illustrates an implant 20' formed of twisted or braided fibers 103a, 103b. While a single type fiber could be used, the embodiment can be formed of two different fibers 103a, 103b braided or twisted together. One fiber 103a may be provided for encouraging fibrotic response. Such a fiber 103a may be polyester or silk suture material (in which individual fibers 103a may be formed of braided or twisted elements). The other fiber 103b may be a bio-resorbable fiber (e.g., bio-resorbable suture material which may include natural materials such as collagen or synthetic materials such as the PDS suture material). Alternatively, the second fiber 103b may be a non-resorbable material such as polypropylene suture material to provide added stiffness to the implant. The fibers 103a, 103b may be bonded together along the axial length of the implant 102' to provide added stiffness.

Figure 12:
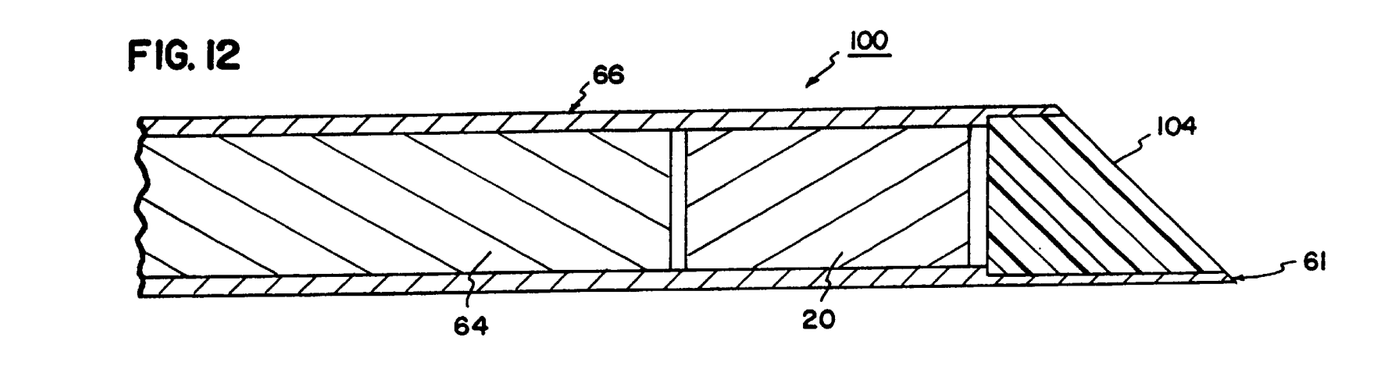
FIG. 12 is a side-sectional view of a delivery system for placing an implant in the soft palate.
Figure 13:
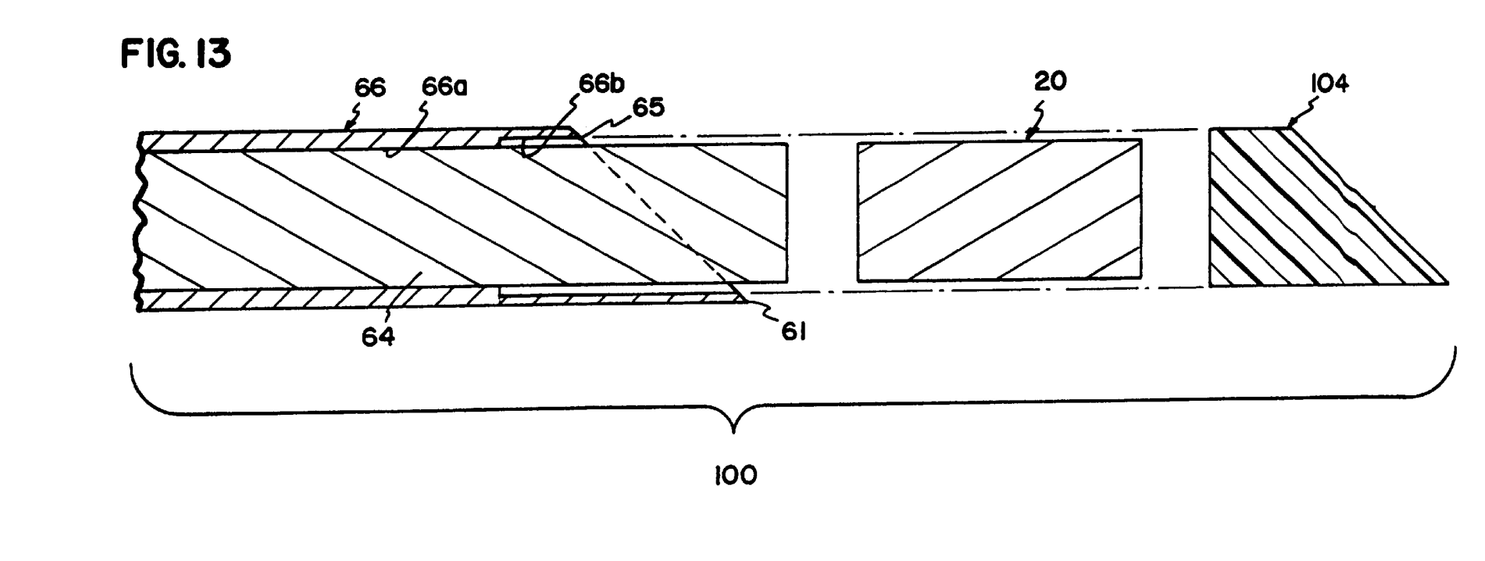
FIG. 13 is an exploded view of FIG. 12 following delivery of the implant from the delivery system.
Figures 14, 15, 16:
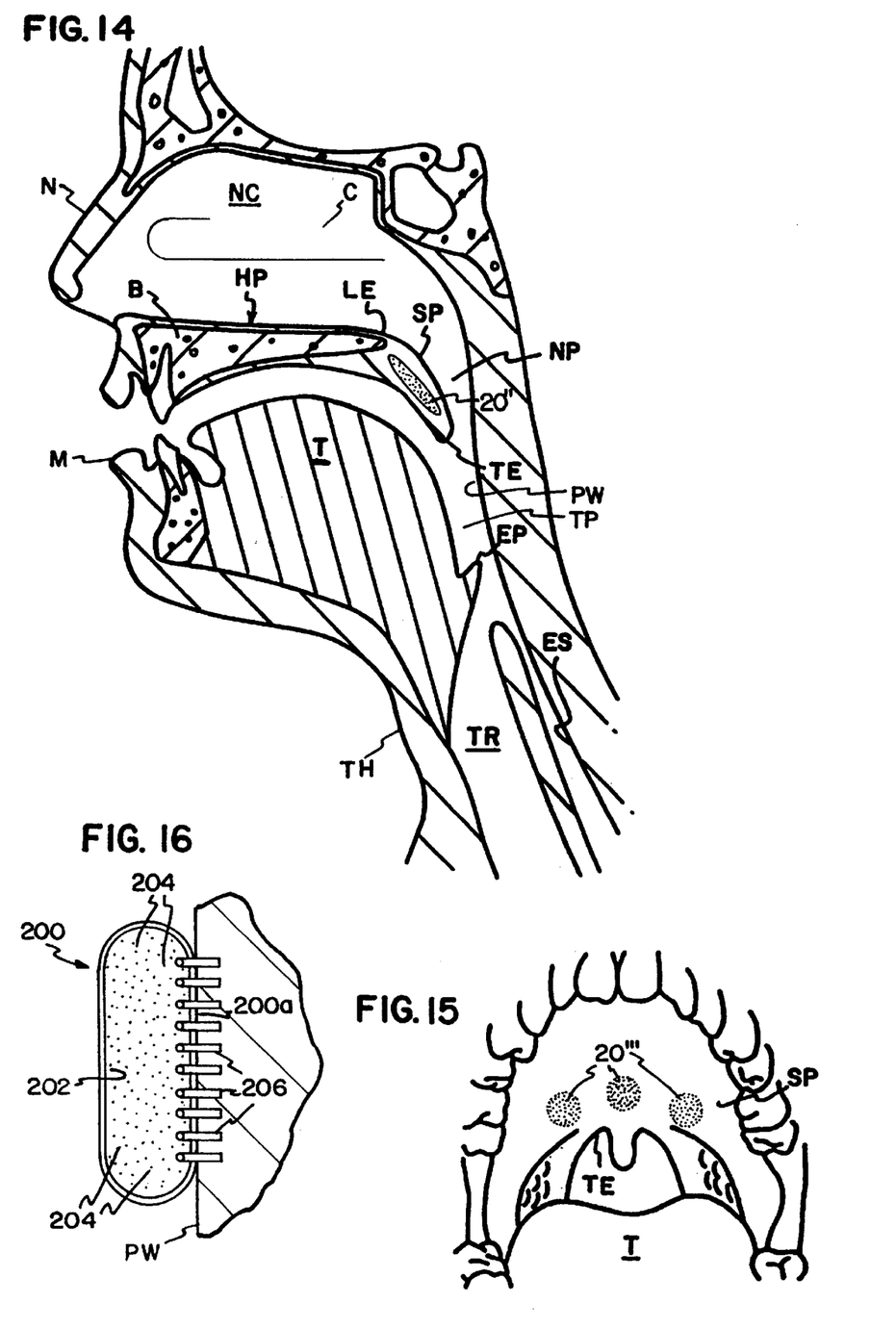
FIG. 14 is the view of FIG. 1 with the soft palate containing an implant in the form of a bolus of micro-beads deposited in a linear path.
FIG. 15 is the view of FIG. 3 showing micro-beads deposited as spherical deposits.
FIG. 16 is a schematic representation showing a patch for delivering a bolus of micro-beads through a plurality of needles.

FIGS. 12 and 13 show a delivery system 100 for placing an implant in the soft palate SP. FIGS. 13–15 illustrate use of the novel delivery system 100 with a strip implant 20 (such as implant 20' of FIG. 11).

A needle 66 is provided having a ground beveled distal tip 61 for piercing tissue of the soft palate. The needle 66 is hollow and carries the implant 20 in sliding close tolerance. A rod 64 is slidably positioned in the needle 66 proximal to the implant 20. The implant 20 is carried by the needle 66 to a desired implant site within the soft palate. At the desired site, the implant 20 is deployed by retracting the needle 66 while holding the rod 64 in place. Relative movement between the rod 64 and needle 66 causes the rod 64 to dispel the implant 20 from the needle 66 without need for moving the implant 20 relative to the soft palate.

While advancing the needle 66 through the soft palate, tissue and body fluids may be inclined to enter the needle 66 and later interfere with discharge of the implant 102 from the needle 66. An optional plug 104 is provided to prevent admission of tissue into the needle 66. The plug 104 is a bio-resorbable material. During discharge, the rod 64 (due to retraction of the needle 66) urges both the plug 104 and implant 20 out of the needle 66. Since the plug 104 is bio-resorbable, it resorbs into the patient's body over time. The implant 20 provides the therapeutic effect described above with reference to altering the dynamic response of the soft palate.

To avoid the plug 104 being urged proximally into the needle 66, the needle 66 includes a first bore 66a having a diameter approximate to that of the rod 64 and implant 20 and a second bore 66b at the distal tip 61. The second bore 66b is coaxial with the first bore 66a and is larger than the first bore 66a so that an annular retaining edge 65 is defined within the needle 66. The plug 104 abuts the retaining edge 65 and is restricted from being urged into the needle 66 as the needle 66 is advanced through the tissue of the soft palate.

The needle 66 may be porous at the distal tip 61 so the needle with a loaded implant 20 may be soaked for sterilization if so desired.

C. Bolus of Particulate Matter

FIGS. 14 and 15 show an implant 20" as a bolus of particulate matter. An example of such particulate matter would be micro-beads. An example of such is taught in U.S. Pat. Nos. 5,792,478 and 5,451,406. These patents teach carbon-coated metallic or ceramic particles having cross-sectional dimensions of between 100 and 1,000 microns. The particles are carried in a fluid or gel. These patents state that upon insertion into body tissue, the particles do not migrate significantly and, apparently due to fibrotic response, the tissue into which the particles are injected stiffens.

The particles of U.S. Pat. Nos. 5,792,478 and 5,451,406 are one example of particles for stiffening injection. Such particles can also include ceramic particles or pure carbon or other bio-compatible particles. For example, the particles can be vitreous carbon, zirconia (ZrO2), alumina (Al2O3) or polymeric. The particles can be carried in a liquid or gel medium. The particles can have multi-modal particle size distributions (i.e., a mix of two or more sizes of particles with the smaller particles filling interstitial spaces between larger particles).

The bolus 20" of particles can be applied by a needle to inject the bolus 20" into the soft palate SP. The bolus can be the same volume as the volume of the implants 20 of FIGS. 8 and 9. With reference to FIG. 15, a multiple of bolus injections can be made in the soft palate resulting in deposition of generally spherical deposits 20'" of particles. Alternatively, an injecting needle can be withdrawn while simultaneously ejecting particles for the bolus 20" (FIG. 14) to be deposited in a line similar in dimensions to the implants 20 of FIGS. 8 and 9.

The foregoing emphasizes the use of implants to stiffen the soft palate SP. Implants 20" can be placed in any of the tissue of the naso-pharyngeal area (e.g., the concha C or other nasal mucosal surface, soft palate SP or pharyngeal wall PW—lateral or posterior) to treat snoring. Also, such a treatment can stiffen the tissue of the throat and treat sleep apnea resulting from airway collapse by stiffening the airway.

While a needle deposition of a bolus of particles is presently most preferred, the bolus can be applied in other manners. FIG. 16 illustrates deposition of particulates through a patch 200 having a volume 202 containing such micro-beads 204. One side 200a of the patch 200 contains an array of micro-needles 206 communicating with the volume 202. The needles 206 may be small diameter, shallow penetration needles to minimize pain and blood.

Examples of shallow, small diameter needles are shown in U.S. Pat. No. 5,582,184 to Erickson et al. Placing the surface 200a against the tissue (e.g., the pharyngeal wall PW as shown in FIG. 16), the needles 206 penetrate the outer surface of the tissue PW. The patch 200 can then be compressed (by finger pressure, roller or the like) to eject the beads 204 from the volume 202 through the plurality of needles 206. The patch 200 can be provided with interior dividing walls (not shown) so that some of the volume of beads 204 is ejected through each needle 206. In the figures, the thickness of the patch 200 is exaggerated for ease of illustration.

Stiffening of the naso-pharyngeal tissue provided structure to reduce vibration and snoring. Such structure reduces airway collapse as a treatment for sleep apnea.

The foregoing describes numerous embodiments of an invention for an implant for the naso-pharyngeal area to treat an upper airway condition. Having described the invention, alternatives and embodiments may occur to one of skill in the art. It is intended that such modifications and equivalents shall be included within the scope of the following claims.

What is claimed is:

1. A method for treating an upper airway condition of a patient, said method comprising:
    selecting an implant sized to be implanted into a tissue of a pharyngeal wall of said patient, said implant including a longitudinal permanent implant of biocompatible material selected to stiffen said tissue of said pharyngeal wall; and
    implanting said implant into said tissue of said pharyngeal wall to stiffen said tissue.

2. A method according to claim 1 wherein said implant is a braid of biocompatible fibers.

3. A method according to claim 2 wherein said implant material is selected to induce a fibrotic response from said tissue.

4. A method according to claim 1 wherein said implant is a bolus of a particulate material selected for limited migration within said tissue.

5. A method according to claim 4 wherein said implant material is selected to induce a fibrotic response from said tissue.

6. A method according to claim 1/wherein said upper airway condition is sleep apnea.

7. A method for treating an upper airway condition of a patient, said method comprising:
    selecting an implant sized to be implanted into a tissue of a nasal area of said patient, said implant having characteristics for said implant, at least in tissue of said nasal area, to stiffen said tissue of said nasal area; and
    implanting said implant into said tissue of said nasal area to stiffen said tissue.

8. A method according to claim 7 wherein said implant is a braid of biocompatible fibers.

9. A method according to claim 7 wherein said implant is a bolus of a particulate material selected for limited migration within said tissue.

10. A method according to claim 7 wherein said upper airway condition is snoring.

11. A method according to claim 7 wherein said upper airway condition is sleep apnea.

* * * * *